United States Patent [19]

Kuroda et al.

[11] Patent Number: 4,985,325
[45] Date of Patent: Jan. 15, 1991

[54] PHOTOCONDUCTOR FOR ELECTROPHOTOGRAPHY CONTAINING HYDRAZONE

[75] Inventors: Masami Kuroda; Yoshinobu Sugata; Noboru Furusho, all of Kawasaki, Japan

[73] Assignee: Fuji Electric Co., Ltd., Kanagawa, Japan

[21] Appl. No.: 406,807

[22] Filed: Sep. 13, 1989

[30] Foreign Application Priority Data

Sep. 17, 1988 [JP] Japan .................. 63-233104

[51] Int. Cl.$^5$ .............................. G03G 5/14
[52] U.S. Cl. ........................ 430/59; 252/500
[58] Field of Search ............... 430/59; 282/500

[56] References Cited

U.S. PATENT DOCUMENTS

| | | | |
|---|---|---|---|
| 4,150,987 | 8/1979 | Anderson et al. | 430/59 |
| 4,353,971 | 8/1982 | Chang et al. | 430/58 |
| 4,367,273 | 1/1983 | Murayama et al. | 430/56 |
| 4,385,106 | 11/1983 | Sakai | 430/59 |
| 4,415,640 | 11/1983 | Goto et al. | 430/59 |
| 4,448,868 | 10/1984 | Suzuki et al. | 430/58 |
| 4,565,761 | 11/1986 | Katagiri et al. | 430/83 |
| 4,568,623 | 2/1986 | Inakino et al. | 430/58 |
| 4,606,986 | 8/1986 | Yanus et al. | 430/59 |
| 4,624,904 | 11/1986 | Kazmaier et al. | 430/59 |
| 4,629,670 | 12/1986 | Katagiri et al. | 430/58 |
| 4,666,809 | 5/1987 | Matsumoto et al. | 430/76 |
| 4,673,630 | 8/1987 | Katagiri et al. | 430/72 |
| 4,677,045 | 2/1987 | Champ et al. | 430/76 |
| 4,702,983 | 10/1987 | Haine et al. | 430/75 |
| 4,731,315 | 7/1988 | Hori et al. | 430/77 |
| 4,783,387 | 11/1988 | Meda | 430/76 |
| 4,808,503 | 2/1989 | Yamada et al. | 430/75 |
| 4,839,252 | 7/1989 | Murata et al. | 430/59 |
| 4,861,691 | 7/1989 | Kuroda et al. | 430/59 |
| 4,861,692 | 1/1989 | Kuroda et al. | 430/59 |

FOREIGN PATENT DOCUMENTS 59-182457  7/1984  Japan .
59-182456  9/1984  Japan .

*Primary Examiner*—David Welsh
*Attorney, Agent, or Firm*—Spencer & Frank

[57] ABSTRACT

A photoconductor for electrophotography comprises a substrate and a photosensitive layer formed thereon and including a novel hydrazone compound as a charge transporting substance. The hydrazone compound is represented by the following general formula:

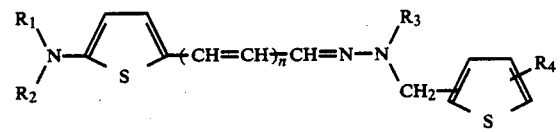

wherein, each of $R_1$, $R_2$ and $R_3$ stands for any one of an alkyl group, an alkenyl group, an aralkyl group and an aryl group, which groups may be or not may be substituted, $R_4$ stands for any one of a hydrogen atom, a halogen atom, an alkyl group, an alkenyl group, an aralkyl group and an aryl group, which groups may be or not may be substituted an n stands for an integer of 0 to 1.

15 Claims, 1 Drawing Sheet

MISSING PAGE TEMPORARY NOTICE

PATENT # 4985325 FOR ISSUE DATE 1-15-1991 HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 1/2

MISSING PAGE TEMPORARY NOTICE

PATENT # 4985325 FOR ISSUE DATE 1-15-1991 HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 3/4 drazone compounds represented by the general formulae (V) in a binder resin.

The photosensitive layer may comprise a laminate of a charge transporting layer including a charge transporting substance selected from hydrazone compounds represented by the general formulae (V) and a charge generating layer.

The above and other objects, effects, features and advantages of the present invention will become more apparent from the following description of embodiments thereof taken in conjunction with the accompanying drawings.

DETAILED DESCRIPTION OF PREFERRED EMBODIMENTS

The photoconductor according to the present invention contains a specific hydrazone compound in the photosensitive layer thereof. The hydrazone compounds used in the present invention is explained later. The photoconductor may be in the form of any one of the structures of FIGS. 1, 2 and 3, depending on the way of application of the hydrazone compound thereto.

Figure 1:
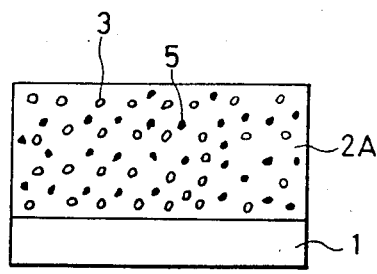
FIGS. 1 to 3 are schematic cross-sectional views of photoconductors according to the present invention, respectively.
Figure 2:
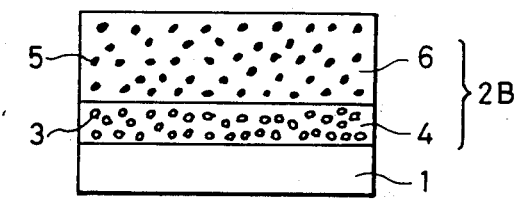
Figure 3:
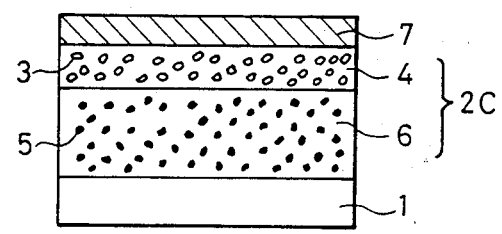

FIGS. 1, 2 and 3 are schematic cross-sectional views of different embodiments of the photoconductor of the present invention, respectively.

FIG. 1 shows a monolayer type photoconductor. A photosensitive layer 2A is provided on an electroconductive substrate 1. The photosensitive layer 2A comprises a charge generating substance 3 and a specific hydrazone compound as a charge transporting substance 5 both of which substances are dispersed in a resin binder matrix so that the photosensitive layer 2A functions as photoconductor.

FIG. 2 shows a laminate type photoconductor. A laminated photosensitive layer 2B is provided on an electroconductive substrate 1, a lower layer of the laminate is a charge generating layer 4 including a charge generating substance 3 as the main component and an upper one is a charge transporting layer 6 containing a specific hydrazone compound as a charge transporting substance 5, so that the photosensitive layer 2B functions as a photoconductor. This photoconductor is usually used according to the negative charge mode.

FIG. 3 shows another laminate type photoconductor having a layer structure in reverse to that of FIG. 2. A laminated photosensitive layer 2C is provided on an electroconductive substrate 1, a lower layer of the laminate is a charge transporting layer 6 including a specific hydrazone compound as a charge transporting substance 5 and an upper one is a charge generating layer 4 including a charge generating substance 3. The photosensitive layer also functions as a photoconductor. This photoconductor is usually used according to the positive charge mode. In this case, a covering layer 7 may generally be further provided as shown in FIG. 3 to protect the charge generating layer 4.

Thus, there are two different types of layer structures in the photoconductor. The reason for this is that, even if any photoconductor with the layer structure as shown in FIG. 2 is to be used in the positive charge mode, no charge transporting substances adaptable to the positive charge mode have been found yet. Accordingly, when the positive charge mode is adapted, the photoconductor is required of a layer structure as shown in FIG. 3 at present.

A photoconductor as shown in FIG. 1 can be produced by dispersing a charge generating substance in a solution of a specific hydrazone compound as a charge transporting substance and a resin binder and applying the resulting dispersion on an electroconductive substrate.

A photoconductor as shown in FIG. 2 can be prepared by depositing a charge generating substance on an electroconductive substrate by means of vacuum evaporation or applying and drying a dispersion of a particulate charge generating substance in a solvent and/or a resin binder on an electroconductive substrate, followed by applying a solution of a specific hydrazone compound as a charge transporting substance and a resin binder on the resulting layer and drying.

A photoconductor as shown in FIG. 3 can be prepared by applying and drying a solution of a specific hydrazone compound as a charge transporting substance and a resin binder on an electroconductive substrate, and depositing a charge generating substance on the resulting coating layer by means of vacuum evaporation or coating and drying a dispersion of a particulate charge generating substance in a solvent and/or a resin binder on the coating layer, followed by formation of a covering layer.

The electroconductive substrate 1 serves as an electrode of the photoconductor and as a support for a layer or layers formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of a particulate charge generating substance 3 in a resin binder or by deposition of a charge generating substance by means of vacuum evaporation, or the like technique as described above, and this layer generates an electric charge upon receiving light. It is important that the charge generating layer 4 be high not only in charge generating efficiency but also in capability of injecting the generated electric charge into the charge transporting layer 6 and any covering layer 7, whose capability is desirably as little dependent upon the electric field as possible and high even in low intensity electric fields. Usable charge generating substances include metal-free phthalocyanine, phthalocyanine compounds such as titanyl phthalocyanine; various azo, quinone and indigo pigments; dyes such a cyanine, squarylium, azulenium, and pyrylium compounds; and selenium and selenium compounds. Among them, a suitable compound can be chosen depending on the wavelength range of a light source used for the image formation. The thickness of the charge generating layer is determined depending on the extinction coefficient of a charge generating substance to be used therein in view of the layer's function of generating an electric charge, but is generally 5 $\mu m$ or smaller, preferably 1 $\mu m$ or smaller. It also is possible to form a charge generating layer using a charge generating substance as a main component in mixture with a charge transporting substance and so on. Resin binders usable in the charge generating layer include polycarbonates, polyesters, polyamides, polyurethanes, epoxy resins, silicone resins, and methacrylate homopolymer and copolymers, which may be used either alone or in an appropriate composition ratio.

The charge transporting layer 6 is a coating film containing a hydrazone compound as an organic charge transporting substance in a resin binder. The hydrazone compound is selected from one of compounds represented by the general formulae (I)-(V), which are described later. The charge transporting layer serves as an insulator layer in the dark so as to retain the electric charge of the photoconductor, and fulfills a function of transporting an electric charge injected from the charge generating layer upon receiving light. Resin binders usable in the charge transporting layer include polycarbonates, polyesters, polyamides, polyurethanes, epoxy resins, silicone resins, and methacryate homopolymer and copolymers.

The covering layer 7 has a function of receiving and retaining an electric charge generated by corona discharge in the dark and a capability of transmitting light to which the charge generating layer should respond. It is necessary that the covering layer transmits light upon exposure of the photoconductor and allows the light to reach the charge generating layer, and then undergoes the injection of an electric charge generated in the charge generating layer to neutralize and erases a surface electric charge. Materials usable in the covering layer include organic insulating film-forming materials such as polyesters and polyamides. Such organic materials may also be used in mixture with an inorganic material such as a glass resin or $SiO_2$, or a material for lowering electric resistance such as a metal or a metallic oxide. Materials usable in the covering layer are not limited to organic insulating materials for film-forming, and further include inorganic materials such as $SiO_2$, metals, and metallic oxides, which may be formed into a covering layer by an appropriate method such as vacuum evaporation and deposition, or sputtering. From the viewpoint of the aforementioned description, it is desirable that the material to be used in the covering layer be as transparent as possible in the wavelength range in which the charge generating substance attains maximum light absorption.

Although the thickness of the covering layer depends on the material or composition thereof, it can be arbitrarily set in so far as it does not produce any adverse effects including an increase in a residual potential in continuous repeated use.

The hydrazone compounds to be used in the present invention include five groups of compounds.

The first group of hydrazone compound to be used in the present invention is represented by the following general formula (I).

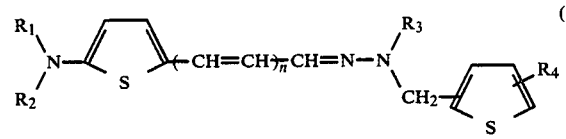

Wherein, each of $R_1$, $R_2$ and $R_3$ stands for any one of an alkyl group, an alkenyl group, an aralkyl group and an aryl group, which groups may be or not may be substituted, $R_4$ stands for any one of a hydrogen atom, a halogen atom, an alkyl group, an alkenyl group, an aralkyl group and an aryl group, which groups may be or not may be substituted and n stands for an integer of 0 or 1.

The second group of hydrazone compound to be used in the present invention is represented by the following general formula (II).

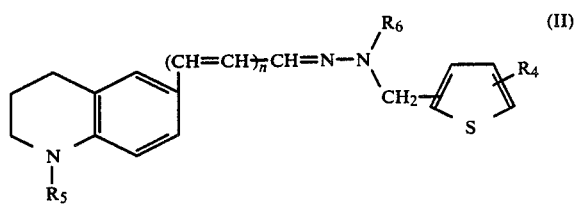

Wherein, $R_4$ stands for any one of a hydrogen atom, a halogen atom, an alkyl group, an alkenyl group, an aralkyl group and an aryl group, which groups may be or not may be substituted, $R_5$ stands for any one of a hydrogen atom, an alkyl group, an alkenyl group, an aralkyl group, an aryl group and a thenyl group, which groups may be or not may be substituted, $R_6$ stands for any one of a hydrogen atom, an alkyl group, an alkenyl group, an aralkyl group and an aryl group, which groups may be or not may be substituted and n stands for an integer of 0 or 1.

The third group of hydrazone compound to be used in the present invention is represented by the following general formula (III).

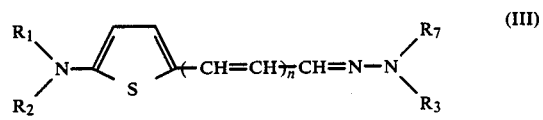

Wherein, each of $R_1$, $R_2$, $R_3$ and $R_7$ stands for any one of an alkyl group, an alkenyl group, an aralkyl group and an aryl group, which groups may be or not may be substituted and n stands for an integer of 0 or 1.

The fourth group of hydrazone compound to be used in the present invention is represented by the following general formula (IV).

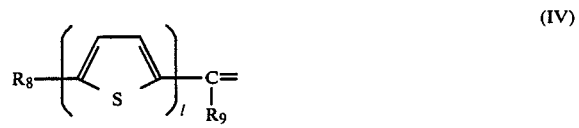

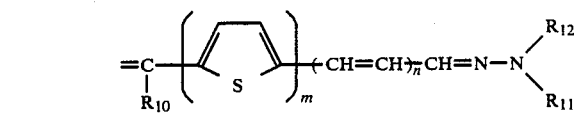

Wherein, each of $R_8$, $R_9$ and $R_{10}$ stands for any one of a hydrogen atom, a halogen atom, an alkoxy group, a nitro group, an alkyl group, an alkenyl group, an aralkyl group, an aryl group and an amino group, last five groups of which may be or not may be substituted, each of $R_{11}$ and $R_{12}$ stands for any one of an alkyl group, an alkenyl group, an aralkyl group, an aryl group and a thenyl group, which groups may be or not may be substituted, each of l and m stands for any one of an integer of 1 or 2 and n stands for an integer of 0 or 1.

The fifth group of hydrazone compound to be used in the present invention is represented by the following general formula (V).

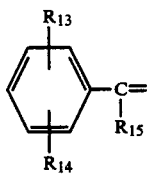

(V)

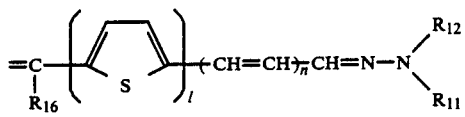

Wherein, each of $R_{11}$ and $R_{12}$ stands for any one of an alkyl group, an alkenyl group, an aralkyl group, an aryl group and a thenyl group, which groups may be or not may be substituted, each of $R_{13}$, $R_{14}$, $R_{15}$ and $R_{16}$ stands for any one of a hydrogen atom, a halogen atom, a hydroxy group, an alkoxy group, a nitro group, an alkyl group, an alkenyl group, an aralkyl group, an aryl group and an amino group, last five groups of which may be or not may be substituted, l stands for an integer of 1 or 2 and n stands for an integer of 0 or 1.

The hydrazone compounds represented by above-mentioned general formulae (I) to (V) can be easily synthesized by a customary method, that is, by condensation reacting aldehydes with hydrazines in an appropriate organic solvent such as an alcohol and under the existence of a small amount of an acid as a condensation agent if necessary.

As for the use of the hydrazone compounds represented by the general formulae given above in photosensitive layers, there has been no precedent before. In the course of the intensive study of various organic materials as made in an attempt of achieve the above object, the present inventors conducted a number of experiments with those hydrazone compounds and, as a result, found that the use of such specific hydrazone compounds represented by the above general formulae (I) to (V) as charge transporting substances is very effective in improving electrophotographic characteristics. Based on this finding, photoconductors having a high sensitivity and good repeated use characteristics are obtained.

Specific examples of the hydrazone compounds of the general formula (I) prepared in the above-mentioned manner include:

| | Compound |
|---|---|
| | No 1 |
| | No 2 |
| | No 3 |
| | No 4 |

| | Compound |
|---|---|
| 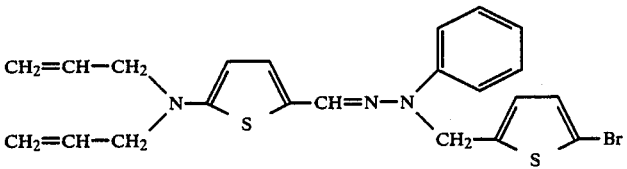 | No 5 |
| 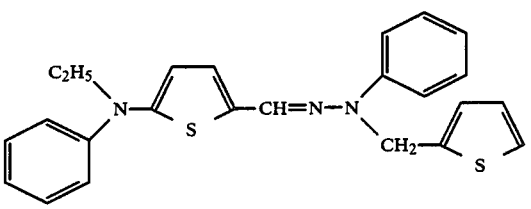 | No 6 |
| 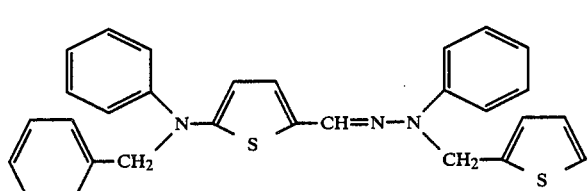 | No 7 |
| 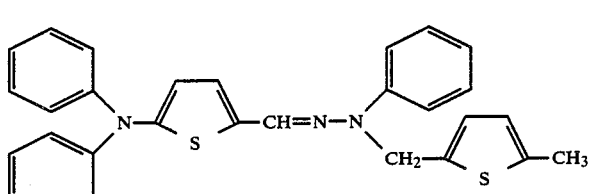 | No 8 |
| 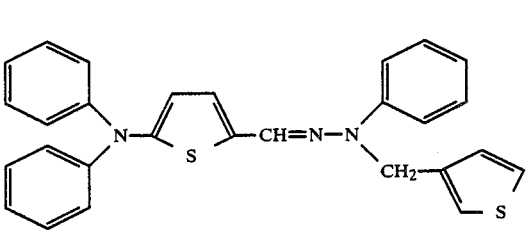 | No 9 |
| 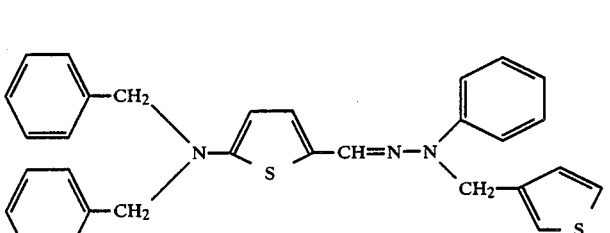 | No 10 |
| 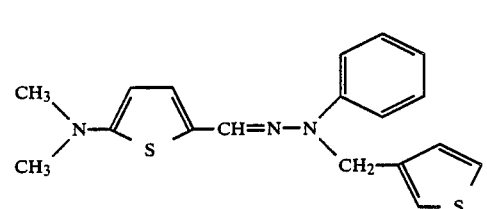 | No 11 |

|     |
| --- |
| -continued |
| Compound No 12 |

Compound No 12: [structure]

Compound No 13: [structure]

Compound No 14: [structure]

Specific examples of the hydrazone compounds of the general formula (II) prepared in the above-mentioned manner include:

Compound No 21: [structure]

Compound No 22: [structure]

-continued
| | Compound |
|---|---|
| 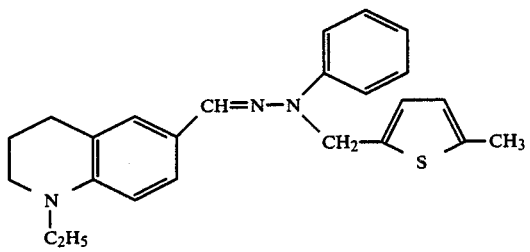 | No 23 |
| 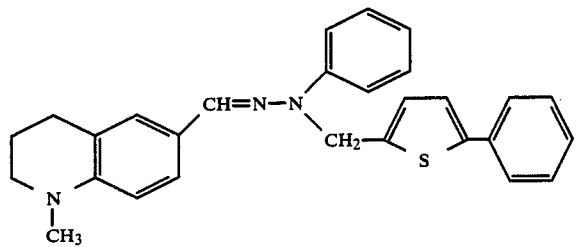 | No 24 |
| 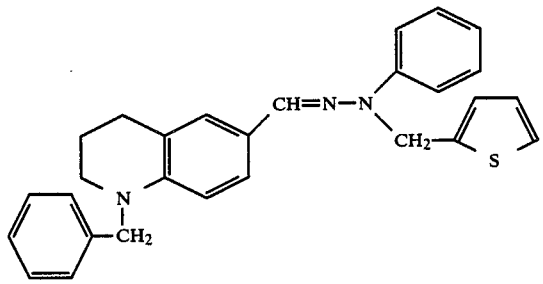 | No 25 |
| 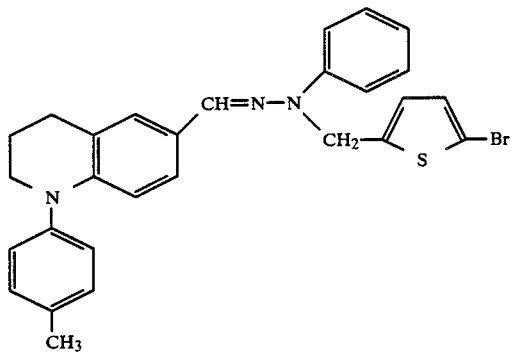 | No 26 |
| 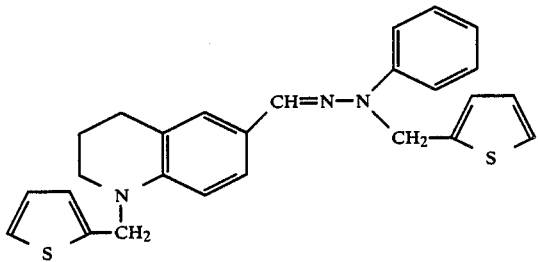 | No 27 |

| -continued | |
|---|---|
| | Compound |
| 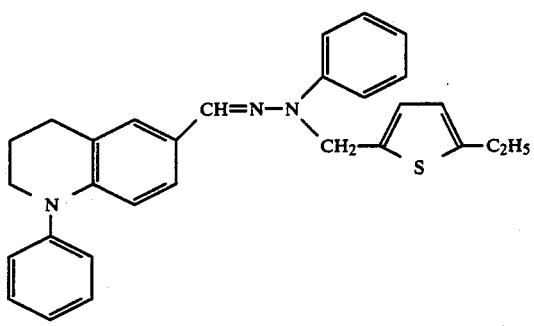 | No 28 |
| 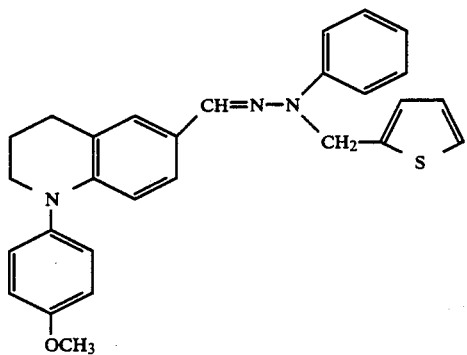 | No 29 |
| 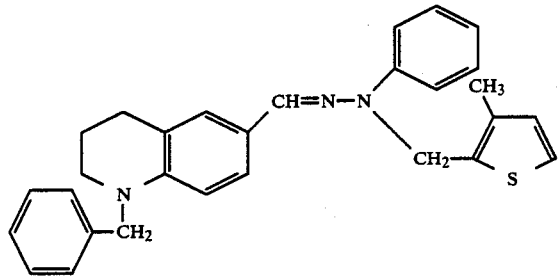 | No 30 |
| 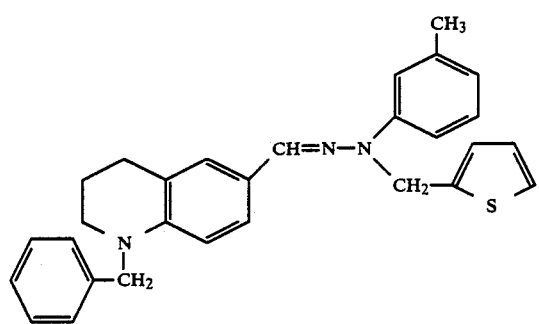 | No 31 |
| 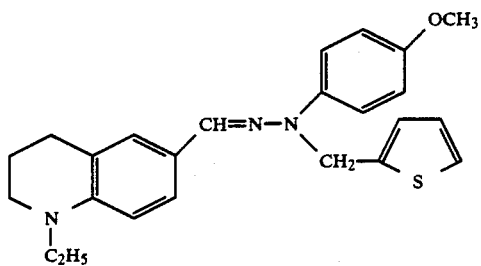 | No 32 |

| | Compound |
|---|---|
| 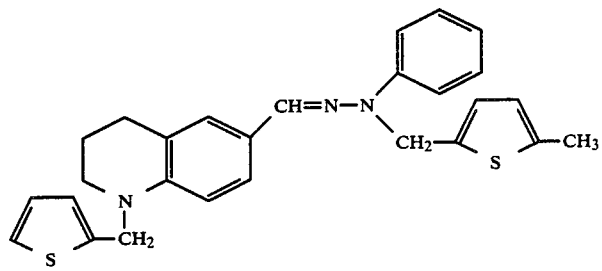 | No 33 |
| 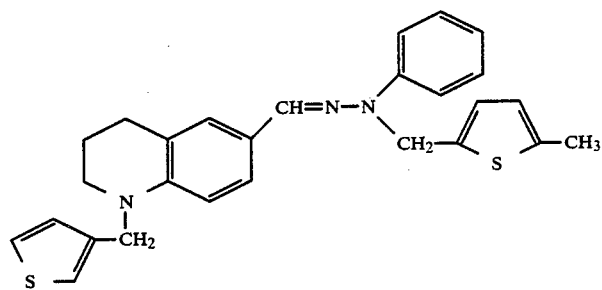 | No 34 |
| 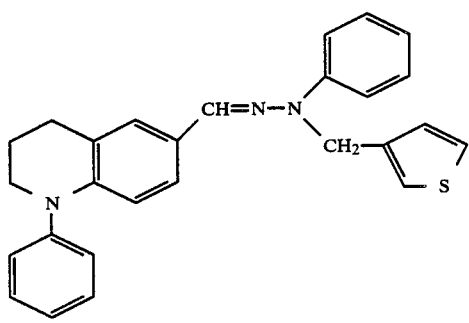 | No 35 |
| 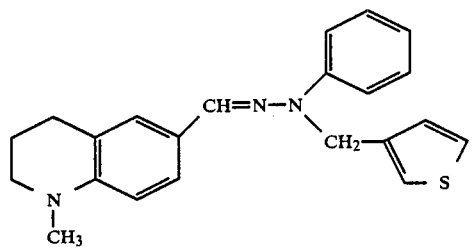 | No 36 |
| 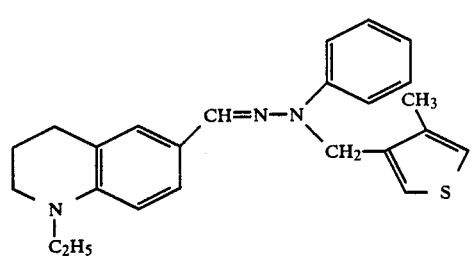 | No 37 |

-continued
| | Compound |
|---|---|
| 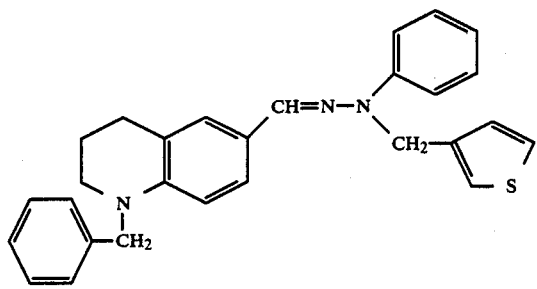 | No 38 |
| 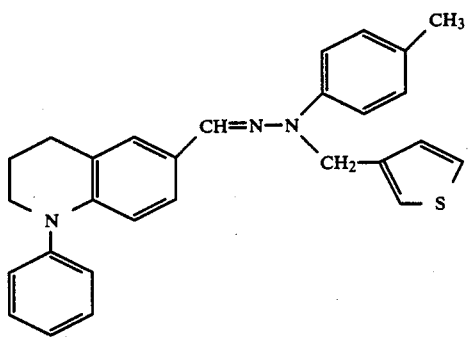 | No 39 |
| 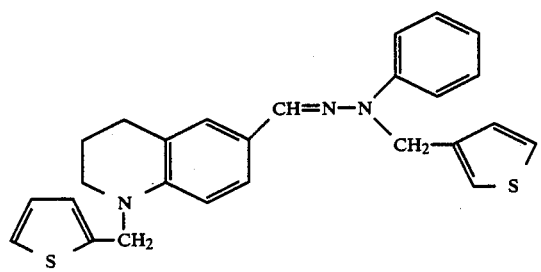 | No 40 |
| 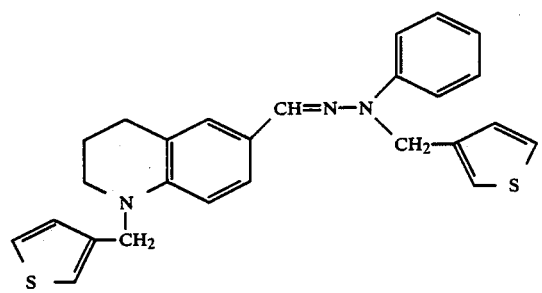 | No 41 |
| 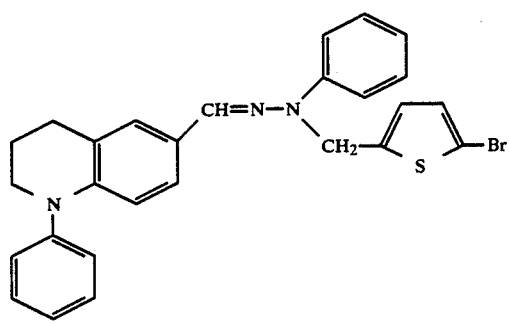 | No 42 |

-continued

| | Compound |
|---|---|
| (structure) | No 43 |
| (structure) | No 44 |
| (structure) | No 45 |
| (structure) | No 46 |
| (structure) | No 47 |

|  | Compound |
|---|---|
| 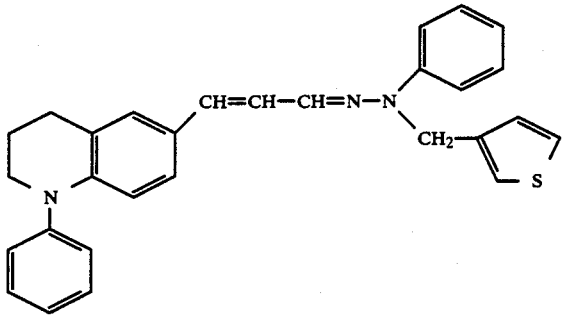 | No 48 |
Specific examples of the hydrazone compounds of the general formula (III) prepared in the above-mentioned manner include:
|  | Compound |
|---|---|
| 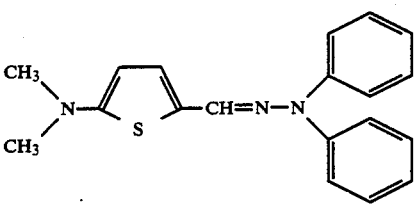 | No 51 |
| 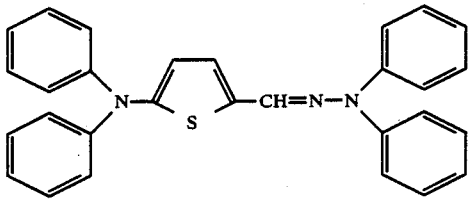 | No 52 |
| 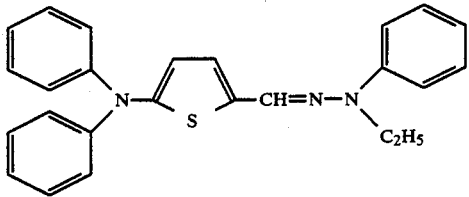 | No 53 |
| 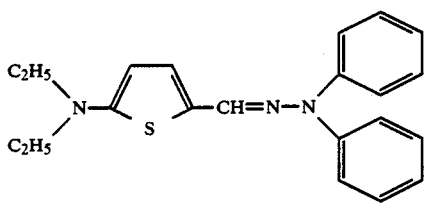 | No 54 |
| 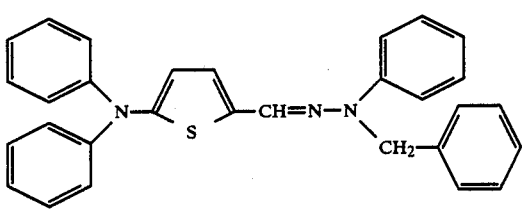 | No 55 |

-continued

| | Compound |
|---|---|
| (structure) | No 56 |
| (structure) | No 57 |
| (structure) | No 58 |
| (structure) | No 59 |
| (structure) | No 60 |
| (structure) | No 61 |
| (structure) | No 62 |

-continued

| | Compound |
|---|---|
| [structure] | No 63 |
| [structure] | No 64 |
| [structure] | No 65 |
| [structure] | No 66 |
| [structure] | No 67 |
| [structure] | No 68 |
| [structure] | No 69 |

-continued
| | Compound |
|---|---|
| 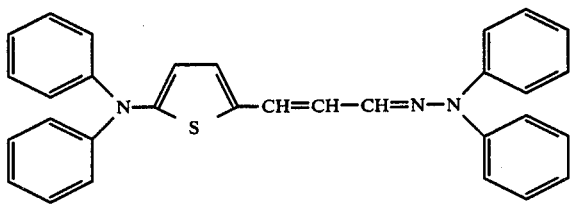 | No 70 |
| 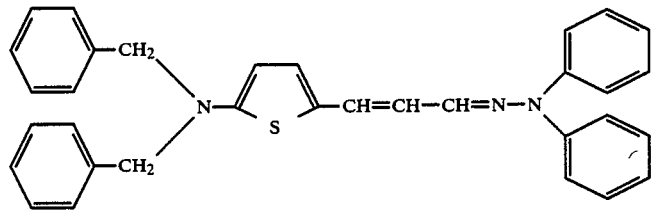 | No 71 |
Specific examples of the hydrazone compounds of the general formula (IV) prepared in the above-mentioned manner include:
| | Compound No |
|---|---|
| 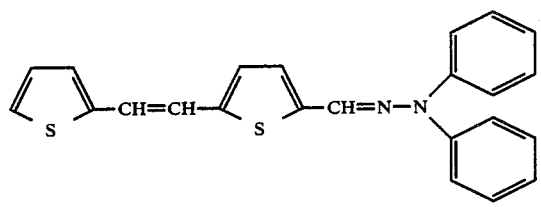 | 81 |
| 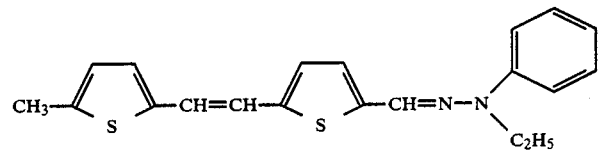 | 82 |
| 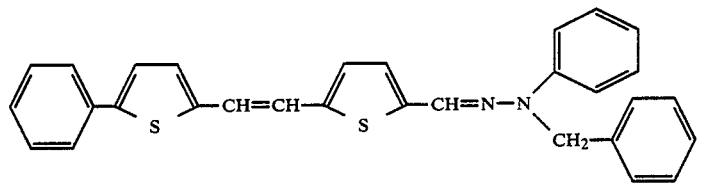 | 83 |
| 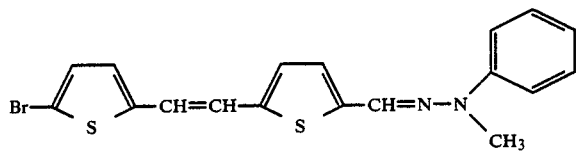 | 84 |
| 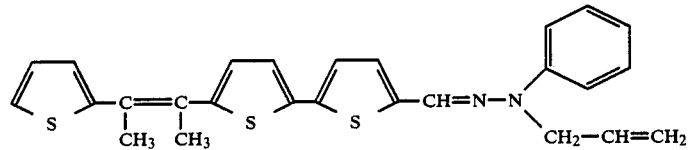 | 85 |

86
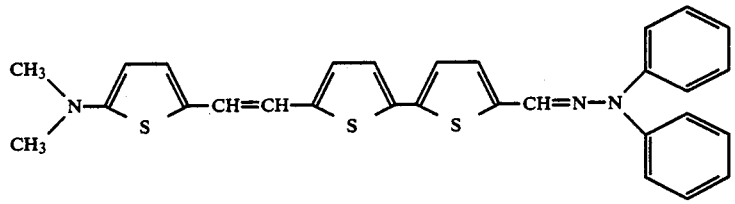
87
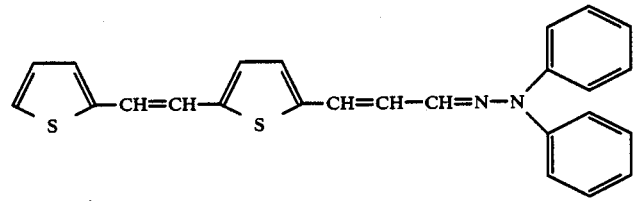
88
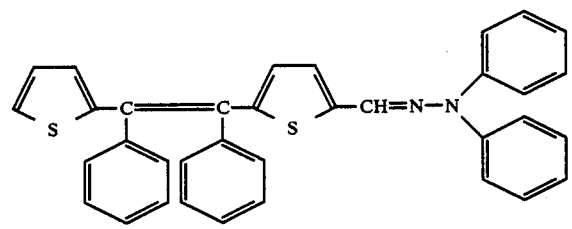
89
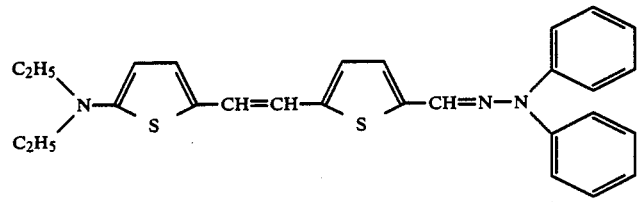
90
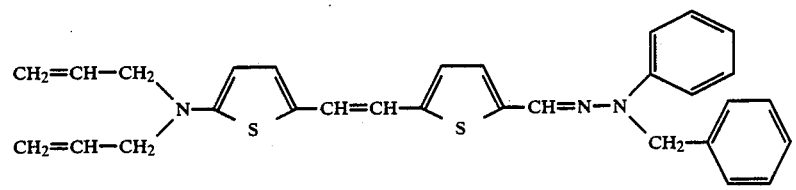
91
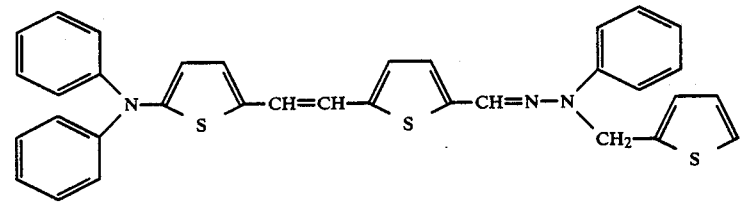
92
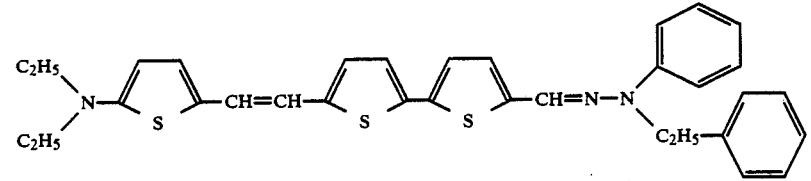

-continued
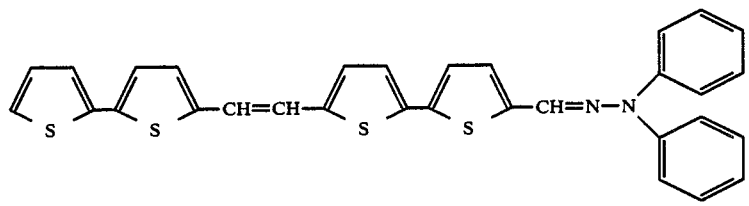
93
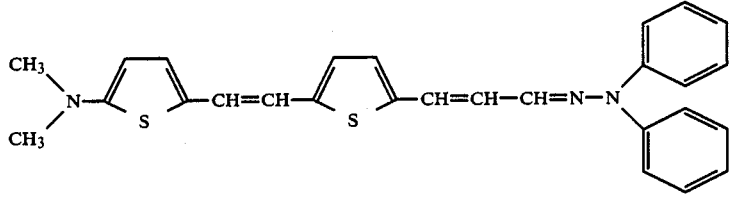
94
Specific examples of the hydrazone compounds of the general formula (V) prepared in the above-mentioned manner include:
Compound No
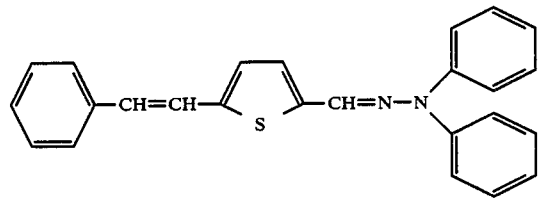
101
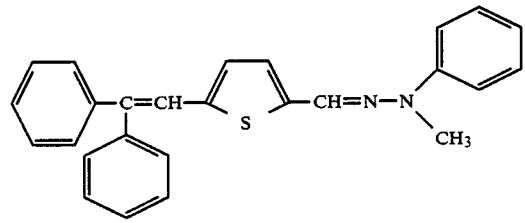
102
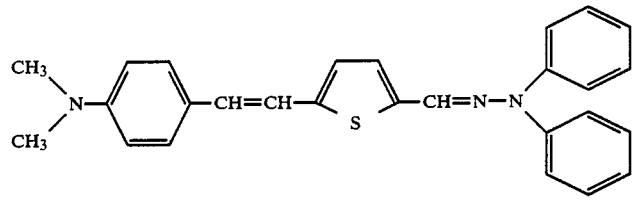
103
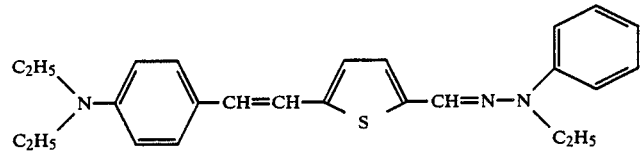
104
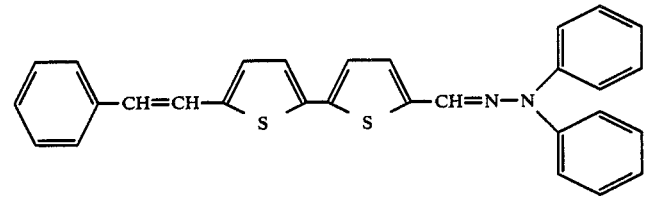
105

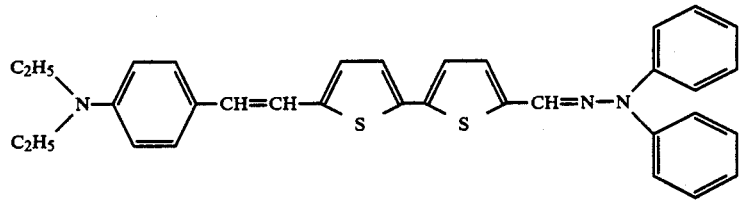
106
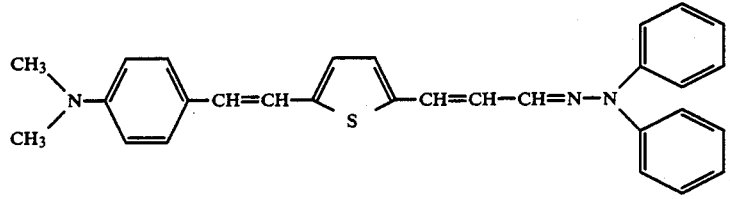
107
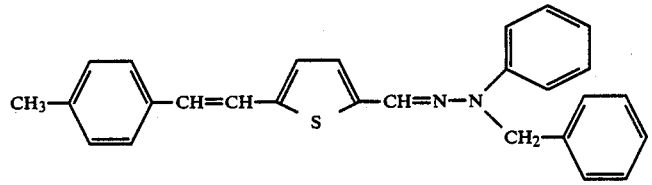
108
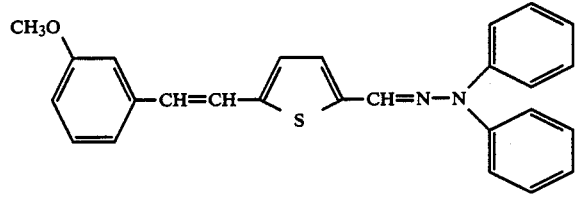
109
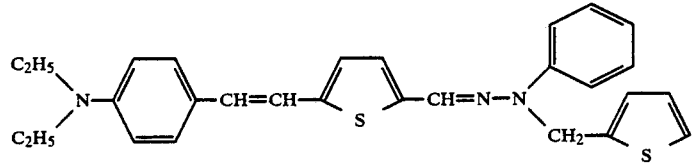
110
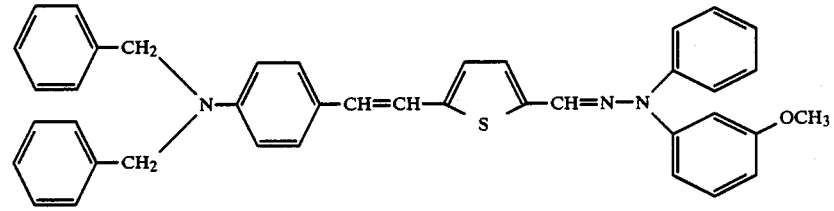
111
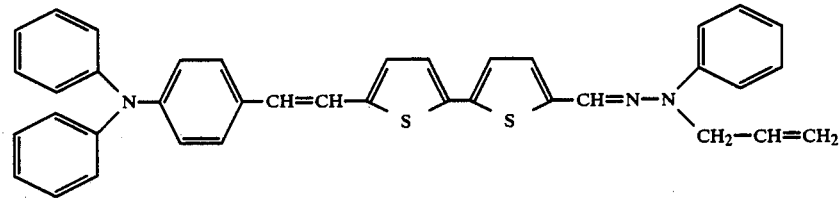
112

-continued
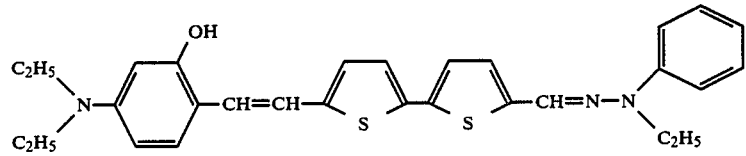 113
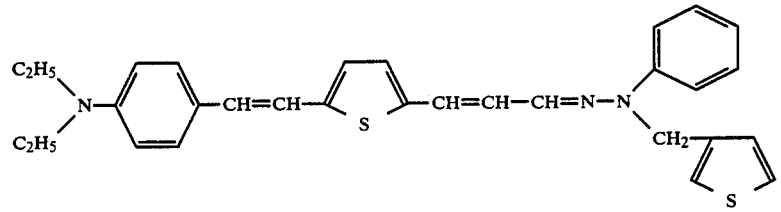 114
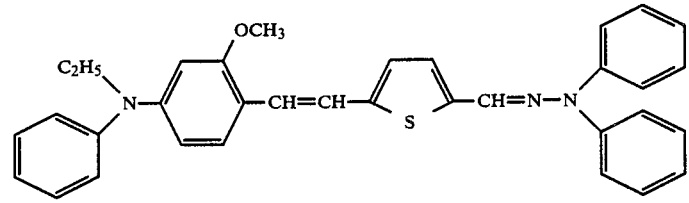 115
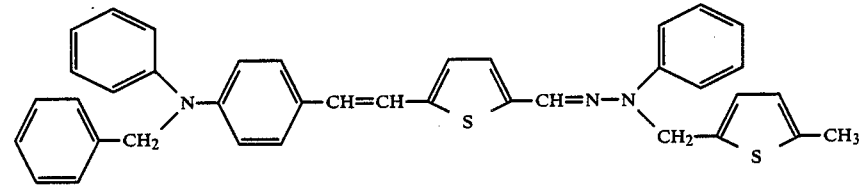 116
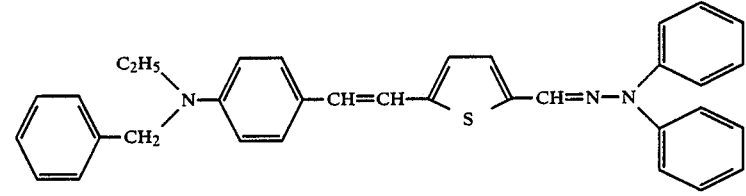 117
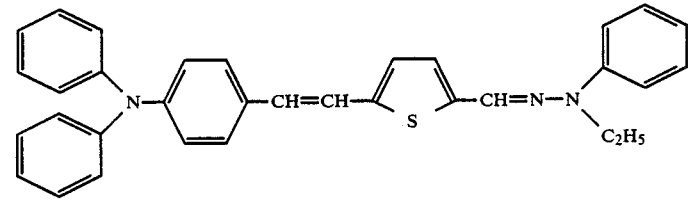 118
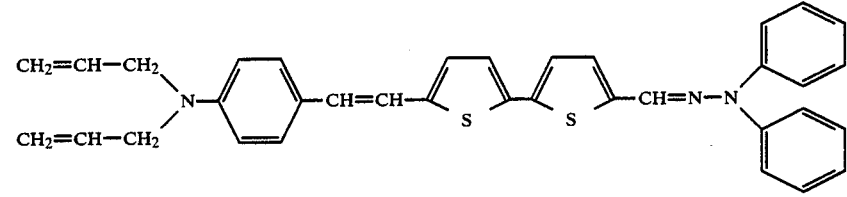 119

-continued

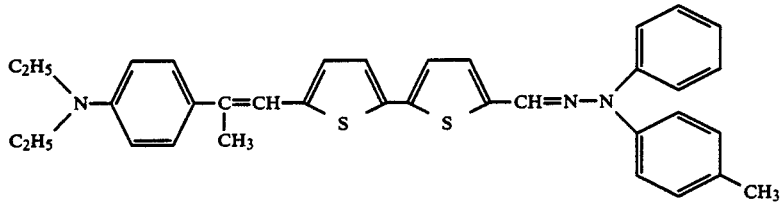

120

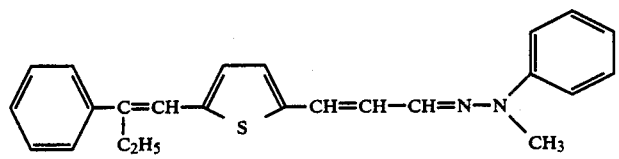

121

The examples of the photoconductor according to the present invention will be explained.

EXAMPLE 1

50 parts by weight of metal-free phthalocyanine (manufactured by Tokyo Kasei Co., Ltd.) pulverized with a ball mill for 150 hours and 100 parts by weight of the hydrazone compound No. 1 mentioned above were kneaded together with 100 parts by weight of a polyester resin (Vylon 200 (trademark), manufactured by Toyobo Co., Ltd.) and tetrahydrofuran (THF) as a solvent with a mixer for 3 hours to prepare a coating liquid. The coating liquid was applied on an aluminum-deposited polyester film (AlPET) as an electroconductive substrate by means of the wire bar technique to form a photosensitive layer having a dry thickness of 15 μm. Thus, a photoconductor with the structure shown in FIG. 1 was produced.

EXAMPLE 2

Metal-free α-phthalocyanine as a starting material was pulverized for 20 minutes into a fine powder with a pulverizer, a LIMMAC (Linear Induction Motor Mixing and Crushing manufactured by Fuji Electric Co., Ltd.) wherein a non-magnetic can containing the metal-free α-phthalocyanine and Teflon pieces as small acting pieces was placed between two linear motors faced each other. The sample of 1 part by weight of the fine powder thus prepared was dispersed in 50 parts by weight of DMF (N,N-dimethylformamide) as a solvent by means of an ultrasonic dispersion treatment. Thereafter, the sample was separated from DMF by filtration and dried to complete the treatment of metal-free phthalocyanine.

80 parts by weight of the hydrazone compound No. 2 mentioned above and 100 parts by weight of polycarbonate resin (Panlite L-1225, manufactured by Teijin Kasei) were solved into methylene chloride to prepare a coating liquid. The coating liquid was applied on an aluminum-deposited polyester film substrate by means of the wire bar technique to form a charge transporting layer having a dry thickness of 15 μm. 50 parts by weight of metal-free phthalocyanine treated in the above-mentioned manner, and 50 parts by weight of a polyester resin (Vylon 200), were kneaded with a mixer for 3 hours together with THF as a solvent to prepare a coating liquid, which was then applied on the charge transporting layer by the wire bar technique to form a charge generating layer having a dry thickness of 1 μm. Thus, a photoconductor with a structure corresponding to that shown in FIG. 3 was produced. A covering layer, which was not directly related to the present invention, was not provided.

EXAMPLE 3

A photoconductor was produced by forming a photosensitive layer in substantially the same manner as in Example 2 except that a squarylium compound represented by the following formula (A) as a charge generating substance and the hydrazone compound No. 3 as a charge transporting substance were used instead of metal-free phthalocyanine and the compound No. 2 in the Example 2, respectively.

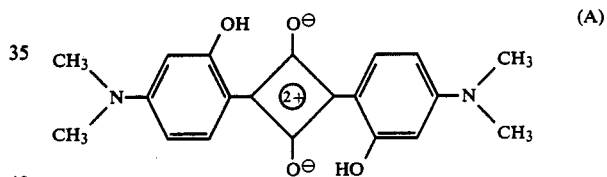

(A)

EXAMPLE 4

A photoconductor was produced by forming a photosensitive layer in substantially the same manner as in Example 2 except the Chlorodiane Blue which is a bisazo pigment disclosed in, for example, Japanese Patent Laid-Open No. 37,543/1972 and the hydrazone compounds No. 4 as a charge transporting substance were used instead of metal-free phthalocyanine and the hydrazone compound No. 2 in the Example 2, respectively.

The electrophotographic characteristics of the four photoconductors thus produced were measured by utilizing an electrostatic recording paper testing apparatus (Kawaguchi Denki Model SP-428).

The surface potential $V_S$ (volts) of each photoconductor is an initial surface potential which was measured when the surface of the photoconductor was positively charged in the dark by corona discharge at +6.0 kV for 10 seconds. After the discontinuation of the corona discharge, the photoconductor was allowed to stand in the dark for 2 seconds, after which the surface potential $V_d$ (volts) of the photoconductor was measured. Subsequently, the surface of the photoconductor was irradiated with white light at an illuminance of 2 luxes and the time (seconds) required for the irradiation to decrease the surface potential of the photoconductor to half of the $V_d$ was measured, then from which time and the illuminance the half decay exposure amount $E_{\frac{1}{2}}$ (lux.sec) was calculated. Also, the surface potential of the photoconductor after 10 seconds of irradiation thereof with white light at an illuminance of 2 luxes was measured as a residual potential $V_r$ (volts). As to the photoconductors of Examples 1-3, a high sensitivity could be expected for light with longer wavelengths. Hence, the electrophotographic characteristics thereof were also measured by using a monochromatic light with a wavelength of 780 nm. Specifically, the $V_s$ and the $V_d$ of each photoconductor were measured in the same manner as described above, and the half decay exposure amount ($\mu J/cm^2$) was found by irradiation of the photoconductor surface with a monochromatic light (wavelength: 780 nm) of 1 $\mu W$ instead of white light, while the residual potential $V_r$ (volts) was measured after 10 seconds of irradiation of the photoconductor surface with the above-mentioned light. The results of the measurements are shown in Table 1.

TABLE 1

| Example No. | White Light | | | Light with Wavelength of 780 nm | | |
|---|---|---|---|---|---|---|
| | $V_s$ (volt) | $V_r$ (volt) | $E_{\frac{1}{2}}$ (lux·sec) | $V_s$ (volt) | $V_r$ (volt) | $E_{\frac{1}{2}}$ ($\mu J/cm^2$) |
| 1 | 630 | 100 | 6.3 | 600 | 80 | 5.1 |
| 2 | 660 | 80 | 4.9 | 680 | 90 | 5.3 |
| 3 | 690 | 70 | 4.7 | 660 | 80 | 5.0 |
| 4 | 630 | 80 | 5.9 | — | — | — |

As can be seen in Table 1, the photoconductors of Examples 1 to 4 were not substantially different therebetween in the half decay exposure amounts and the residual potentials, and showed good surface potential characteristics. The photoconductors of Examples 1 to 3, showed also excellent electrophotographic characteristics for light with a long wavelength of 780 nm. These photoconductors of Examples 1 to 3 can be used for a semiconductor laser printer.

EXAMPLE 5

Selenium was deposited on an aluminum plate having a thickness of 500 $\mu m$ by means of vacuum evaporation to form a charge generating layer having a thickness of 1.5 $\mu m$. A solution of 100 parts by weight of the hydrazone compound No. 5 as mentioned above in 700 parts by weight of tetrahydrofuran (THF) was mixed with a solution of 100 parts by weight of polymethyl methacrylate (PMMA) in 700 parts by weight of toluene to prepare a coating liquid, which was then applied on the charge generating layer by the wire bar technique to form a charge transporting layer having a dry thickness of 20 $\mu m$. Thus, a photoconductor with the structure shown in FIG. 2 was produced. This photoconductor was charged by corona discharge at $-6.0$ kV for 10 second and examined with respect to electrophotographic characteristics to obtain good results, namely $V_s = -620$ V, $V_r = -60$ V and $E_{\frac{1}{2}} = 3.5$ lux.sec.

EXAMPLE 6

50 parts by weight of metal-free phthalocyanine treated in the same manner as in Example 2, 50 parts by weight of vinyl chloride copolymer (MR-110: manufactured by Nihon Zeon) and 50 parts by weight of methylen chloride were kneaded with a mixer for 3 hours to prepare a coating liquid, which was then applied on an aluminum support to form a charge generating layer having a thickness of about 1 $\mu m$. Subsequently, 100 parts by weight of the hydrazone compound No. 6 as mentioned above, 100 parts by weight of a polycarbonate resin (Panlite L-1250), and 0.1 part by weight of a silicone oil were mixed with methylene chloride to prepare a coating liquid, which was then applied on the charge generating layer to form a charge transporting layer having a thickness of about 15 $\mu m$.

The photoconductor thus produced was charged by corona discharge at $-6.0$ kV for 10 second and examined with respect to electrophotographic characteristics in the same manner as in Example 2 to obtain good results, namely $V_s = -680$ V and $E_{\frac{1}{2}} = 4.3$ lux.sec.

EXAMPLE 7

A photoconductor was produced by forming a photosensitive layer in substantially the same manner as in Example 6 except that a bisazo pigment represented by the following formula (B) as a charge generating substance and the hydrazone compound No. 7 as a charge transporting substance were used instead of metal-free phthalocyanine and the compound No. 6 in the Example 6, respectively.

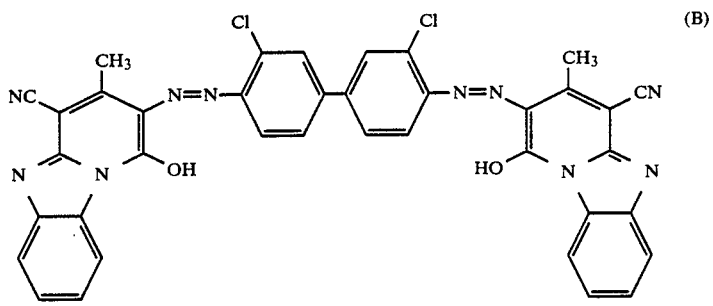

(B)

The photoconductor thus produced was charged by corona discharge at $-6.0$ kV for 10 second and examined with respect to electrophotographic characteristics in the same manner as in Example 5 to obtain good results, namely $V_s = -690$ V and $E_{\frac{1}{2}} = 5.2$ lux.sec.

EXAMPLE 8

Photoconductors were produced in substantially the same manner as in Example 4 except that the hydrazone compounds Nos. 8 to 14 were respectively used instead of the compound No. 4. The results obtained by using the electrostatic recording paper testing apparatus (SP-428) are shown in Table 2. Table 2 shows the half decay exposure amount $E_{\frac{1}{2}}$ (lux.sec) obtained under the experimental conditions where the photoconductors were positively charged in the dark by corona discharge at $+6.0$ kV for 10 seconds and irradiated with white light at an illuminance of 2 luxes.

TABLE 2

| Compound No. | $E_{\frac{1}{2}}$ (lux · sec) |
|---|---|
| 8 | 6.6 |
| 9 | 6.5 |
| 10 | 6.9 |
| 11 | 4.5 |
| 12 | 5.5 |
| 13 | 5.3 |
| 14 | 7.1 |

As can be seen in Table 2, the photoconductors using the respective hydrazone compounds Nos. 8 to 14 were satisfactory with respect to the half decay exposure amount $E_{\frac{1}{2}}$.

EXAMPLE 9

A photoconductor was produced in the same manner as in Example 1 except that the hydrazone compound No. 21 was used instead of the hydrazone compound No. 1.

EXAMPLE 10

A photoconductor was produced in the same manner as in Example 2 except that the hydrazone compound No. 22 was used instead of the hydrazone compound No. 2.

EXAMPLE 11

A photoconductor was produced in the same manner as in Example 3 except that the hydrazone compound No. 23 was used instead of the hydrazone compound No. 3.

EXAMPLE 12

A photoconductor was produced in the same manner as in Example 4 except that the hydrazone compound No. 24 was used instead of the hydrazone compound No. 4.

The electrophotographic characteristics of the photoconductors thus produced are measured by utilizing the testing apparatus SP-428. The measuring conditions are the same as Examples 1 to 4. As to Examples 9 to 11, electrophotographic characteristics are measured with a monochromatic light of wavelength 780 nm. The results obtained are shown in Table 3.

TABLE 3

| Example No. | White Light | | | Light with Wavelength of 780 nm | | |
|---|---|---|---|---|---|---|
| | $V_s$ (volt) | $V_r$ (volt) | $E_{\frac{1}{2}}$ (lux · sec) | $V_s$ (volt) | $V_r$ (volt) | $E_{\frac{1}{2}}$ ($\mu J/cm^2$) |
| 9 | 620 | 80 | 6.8 | 630 | 100 | 7.1 |
| 10 | 630 | 60 | 4.9 | 580 | 70 | 4.6 |
| 11 | 650 | 90 | 4.2 | 660 | 60 | 3.9 |
| 12 | 660 | 100 | 5.7 | — | — | — |

As can be seen in Table 3, the photoconductors of Examples 9 to 12 were not substantially different therebetween in the half decay exposure amounts and the residual potentials, and showed good surface potential characteristics. The photoconductors of Examples 9 to 11, showed also excellent electrophotographic characteristics for light with a long wavelength of 780 nm. These photoconductors of Examples 9 to 11 can be used for a semiconductor laser printer.

EXAMPLE 13

A photoconductor was produced in the same manner as in Example 5 except that the hydrazone compound No. 25 was used instead of the hydrazone compound No. 5. This photoconductor was charged by corona discharge at −6.0 kV for 10 second and examined with respect to electrophotographic characteristics to obtain good results, namely $V_s = -700$ V, $V_r = -60$ V and $E_{\frac{1}{2}} = 3.6$ lux.sec.

EXAMPLE 14

A photoconductor was produced in the same manner as in Example 6 except that the hydrazone compound No. 26 was used instead of the hydrazone compound No. 6.

The photoconductor thus produced was charged by corona discharge at −6.0 kV for 10 second and examined with respect to electrophotographic characteristics in the same manner as in Example 5 to obtain good results, namely $V_s = -600$ V and $E_{\frac{1}{2}} = 3.2$ lux.sec.

EXAMPLE 15

A photoconductor was produced in the same manner as in Example 7 except that the hydrazone compound No. 27 was used instead of the hydrazone compound No. 7.

The photoconductor thus produced was charged by corona discharge at −6.0 kV for 10 second and examined with respect to electrophotographic characteristics in the same manner as in Example 5 to obtain good results, namely $V_s = -710$ V and $E_{\frac{1}{2}} = 4.7$ lux.sec.

EXAMPLE 16

The photoconductors were prepared in the same manner as in Example 4 but the respective hydrazone compound Nos. 28 to 48 were used as a charge transporting substance. The electrophotographic characteristics of these photoconductors were measured with the testing apparatus SP-428. The results obtained are shown in Table 4. Table 4 shows the half decay exposure amounts $E_{\frac{1}{2}}$ (lux.sec) obtained under the experimental conditions where the photoconductors were positively charged in the dark by corona discharge at +6.0 kV for 10 seconds and irradiated with white light at an illuminance of 2 luxes.

TABLE 4

| Compound No. | $E_{\frac{1}{2}}$ (lux · sec) |
|---|---|
| 28 | 5.2 |
| 29 | 6.2 |
| 30 | 6.8 |
| 31 | 4.5 |
| 32 | 5.3 |
| 33 | 6.1 |
| 34 | 7.2 |
| 35 | 6.6 |
| 36 | 5.4 |
| 37 | 5.5 |
| 38 | 6.3 |
| 39 | 6.7 |
| 40 | 6.0 |
| 41 | 4.9 |
| 42 | 5.8 |
| 43 | 5.1 |
| 44 | 6.7 |
| 45 | 5.6 |
| 46 | 6.6 |
| 47 | 5.9 |
| 48 | 5.8 |

As can be seen in Table 4, the photoconductors using the respective hydrazone compounds Nos. 28 to 48 were satisfactory with respect to the half decay exposure amount $E_{\frac{1}{2}}$.

EXAMPLE 17

A photoconductor was produced in the same manner as in Example 1 except that the hydrazone compound No. 51 was used instead of the hydrazone compound No. 1.

EXAMPLE 18

A photoconductor was produced in the same manner as in Example 2 except that the hydrazone compound No. 52 was used instead of the hydrazone compound No. 2.

EXAMPLE 19

A photoconductor was produced in the same manner as in Example 3 except that the hydrazone compound No. 53 was used instead of the hydrazone compound No. 3.

EXAMPLE 20

A photoconductor was produced in the same manner as in Example 4 except that the hydrazone compound No. 54 was used instead of the hydrazone compound No. 4.

The electrophotographic characteristics of the photoconductors thus produced are measured by utilizing the testing apparatus SP-428. The measuring conditions are the same as Examples 1 to 4. As to Examples 17 to 19, electrophotographic characteristics are measured with a monochromatic light of wavelength 780 nm. The results obtained are shown in Table 5.

TABLE 5

| Example No. | White Light | | | Light with Wavelength of 780 nm | | |
|---|---|---|---|---|---|---|
| | $V_s$ (volt) | $V_r$ (volt) | $E_{\frac{1}{2}}$ (lux·sec) | $V_s$ (volt) | $V_r$ (volt) | $E_{\frac{1}{2}}$ (μJ/cm²) |
| 17 | 610 | 110 | 7.0 | 630 | 90 | 7.6 |
| 18 | 600 | 70 | 5.4 | 610 | 60 | 5.8 |
| 19 | 630 | 80 | 3.9 | 650 | 70 | 4.3 |
| 20 | 650 | 90 | 4.2 | — | — | — |

As can be seen in Table 5, the photoconductors of Examples 17 to 20 were not substantially different therebetween in the half decay exposure amounts and the residual potentials, and showed good surface potential characteristics. The photoconductors of Examples 17 to 19, showed also excellent electrophotographic characteristics for light with a long wavelength of 780 nm. These photoconductors of Examples 17 to 19 can be used for a semiconductor laser printer.

EXAMPLE 21

A photoconductor was produced in the same manner as in Example 5 except that the hydrazone compound No. 55 was used instead of the hydrazone compound No. 5. This photoconductor was charged by corona discharge at −6.0 kV for 10 second and examined with respect to electrophotographic characteristics to obtain good results, namely $V_s = -680$ V, $V_r = -50$ V and $E_{\frac{1}{2}} = 4.0$ lux.sec.

EXAMPLE 22

A photoconductor was produced in the same manner as in Example 6 except that the hydrazone compound No. 56 was used instead of the hydrazone compound No. 6.

The photoconductor thus produced was charged by corona discharge at −6.0 kV for 10 second and examined with respect to electrophotographic characteristics in the same manner as in Example 5 to obtain good results, namely $V_s = -630$ V and $E_{\frac{1}{2}} = 3.8$ lux.sec.

EXAMPLE 23

A photoconductor was produced in the same manner as in Example 7 except that the hydrazone compound No. 57 was used instead of the hydrazone compound No. 7.

The photoconductor thus produced was charged by corona discharge at −6.0 kV for 10 second and examined with respect to electrophotographic characteristics in the same manner as in Example 5 to obtain good results, namely $V_s = -650$ V and $E_{\frac{1}{2}} = 3.9$ lux.sec.

EXAMPLE 24

The photoconductors were prepared in the same manner as in Example 4 but the respective hydrazone compound Nos. 58 to 71 were used as a charge transporting substance. The electrophotographic characteristics of these photoconductors were measured with the testing apparatus SP-428. The results obtained are shown in Table 6. Table 6 shows the half decay exposure amounts $E_{\frac{1}{2}}$ (lux.sec) obtained under the experimental conditions where the photoconductors were positively charged in the dark by corona discharge at +6.0 kV for 10 seconds and irradiated with white light at an illuminance of 2 luxes.

TABLE 6

| Compound No. | $E_{\frac{1}{2}}$ (lux · sec) |
|---|---|
| 58 | 5.8 |
| 59 | 7.1 |
| 60 | 5.5 |
| 61 | 6.9 |
| 62 | 7.1 |
| 63 | 5.6 |
| 64 | 4.1 |
| 65 | 4.3 |
| 66 | 6.1 |
| 67 | 5.8 |
| 68 | 6.1 |
| 69 | 6.6 |
| 70 | 5.4 |
| 71 | 6.2 |

As can be seen in Table 6, the photoconductors using the respective hydrazone compounds Nos. 58 to 71 were satisfactory with respect to the half decay exposure amount $E_{\frac{1}{2}}$.

EXAMPLE 25

A photoconductor was produced in the same manner as in Example 1 except that the hydrazone compound No. 81 was used instead of the hydrazone compound No. 1.

EXAMPLE 26

A photoconductor was produced in the same manner as in Example 2 except that the hydrazone compound No. 82 was used instead of the hydrazone compound No. 2.

EXAMPLE 27

A photoconductor was produced in the same manner as in Example 3 except that the hydrazone compound No. 83 was used instead of the hydrazone compound No. 3.

EXAMPLE 28

A photoconductor was produced in the same manner as in Example 4 except that the hydrazone compound No. 84 was used instead of the hydrazone compound No. 4.

The electrophotographic characteristics of the photoconductors thus produced are measured by utilizing the testing apparatus SP-428. The measuring conditions are the same as Examples 1 to 4. As to Examples 25 to 27, electrophotographic characteristics are measured with a monochromatic light of wavelength 780 nm. The results obtained are shown in Table 7.

TABLE 7

| | White Light | | | Light with Wavelength of 780 nm | | |
|---|---|---|---|---|---|---|
| Example No. | $V_s$ (volt) | $V_r$ (volt) | $E_{\frac{1}{2}}$ (lux·sec) | $V_s$ (volt) | $V_r$ (volt) | $E_{\frac{1}{2}}$ ($\mu J/cm^2$) |
| 25 | 620 | 40 | 5.4 | 660 | 70 | 4.9 |
| 26 | 660 | 70 | 6.5 | 640 | 80 | 6.1 |
| 27 | 580 | 80 | 6.1 | 650 | 60 | 5.5 |
| 28 | 630 | 70 | 6.2 | — | — | — |

As can be seen in Table 7, the photoconductors of Examples 25 to 28 were not substantially different therebetween in the half decay exposure amounts and the residual potentials, and showed good surface potential characteristics. The photoconductors of Examples 25 to 27, showed also excellent electrophotographic characteristics for light with a long wavelength of 780 nm. These photoconductors of Examples 25 to 27 can be used for a semiconductor laser printer.

EXAMPLE 29

A photoconductor was produced in the same manner as in Example 5 except that the hydrazone compound No. 85 was used instead of the hydrazone compound No. 5. This photoconductor was charged by corona discharge at −6.0 kV for 10 second and examined with respect to electrophotographic characteristics to obtain good results, namely $V_s = -630$ V, $V_r = -70$ V and $E_{\frac{1}{2}} = 4.5$ lux.sec.

EXAMPLE 30

A photoconductor was produced in the same manner as in Example 6 except that the hydrazone compound No. 86 was used instead of the hydrazone compound No. 6.

The photoconductor thus produced was charged by corona discharge at −6.0 kV for 10 second and examined with respect to electrophotographic characteristics in the same manner as in Example 5 to obtain good results, namely $V_s = -640$ V and $E_{\frac{1}{2}} = 4.9$ lux.sec.

EXAMPLE 31

A photoconductor was produced in the same manner as in Example 7 except that the hydrazone compound No. 87 was used instead of the hydrazone compound No. 7.

The photoconductor thus produced was charged by corona discharge at −6.0 kV for 10 second and examined with respect to electrophotographic characteristics in the same manner as in Example 5 to obtain good results, namely $V_s = -640$ V and $E_{\frac{1}{2}} = 5.2$ lux.sec.

EXAMPLE 32

The photoconductors were prepared in the same manner as in Example 4 but the respective hydrazone compound Nos. 88 to 94 were used as a charge transporting substance. The electrophotographic characteristics of these photoconductors were measured with the testing apparatus SP-428. The results obtained are shown in Table 8. Table 8 shows the half decay exposure amounts $E_{\frac{1}{2}}$ (lux.sec) obtained under the experimental conditions where the photoconductors were positively charged in the dark by corona discharge at +6.0 kV for 10 seconds and irradiated with white light at an illuminance 2 of luxes.

TABLE 8

| Compound No. | $E_{\frac{1}{2}}$ (lux · sec) |
|---|---|
| 88 | 6.2 |
| 89 | 4.2 |
| 90 | 5.6 |
| 91 | 6.1 |
| 92 | 5.8 |
| 93 | 5.4 |
| 94 | 6.3 |

As can be seen in Table 8, the photoconductors using the respective hydrazone compounds Nos. 88 to 94 were satisfactory with respect to the half decay exposure amount $E_{\frac{1}{2}}$.

EXAMPLE 33

A photoconductor was produced in the same manner as in Example 1 except that the hydrazone compound No. 101 was used instead of the hydrazone compound No. 1.

EXAMPLE 34

A photoconductor was produced in the same manner as in Example 2 except that the hydrazone compound No. 102 was used instead of the hydrazone compound No. 2.

EXAMPLE 35

A photoconductor was produced in the same manner as in Example 3 except that the hydrazone compound No. 103 was used instead of the hydrazone compound No. 3.

EXAMPLE 36

A photoconductor was produced in the same manner as in Example 4 except that the hydrazone compound No. 104 was used instead of the hydrazone compound No. 4.

The electrophotographic characteristics of the photoconductors thus produced are measured by utilizing the testing apparatus SP-428. The measuring conditions are the same as Examples 1 to 4. As to Examples 33 to 35, electrophotographic characteristics are measured with a monochromatic light of wavelength 780 nm. The results obtained are shown in Table 9.

TABLE 9

| Example No. | White Light | | | Light with Wavelength of 780 nm | | |
|---|---|---|---|---|---|---|
| | $V_s$ (volt) | $V_r$ (volt) | $E_{\frac{1}{2}}$ (lux·sec) | $V_s$ (volt) | $V_r$ (volt) | $E_{\frac{1}{2}}$ (μJ/cm²) |
| 33 | 640 | 60 | 5.8 | 590 | 60 | 5.3 |
| 34 | 620 | 70 | 5.3 | 630 | 70 | 5.8 |
| 35 | 660 | 60 | 5.6 | 640 | 70 | 5.9 |
| 36 | 610 | 50 | 6.1 | — | — | — |

As can be seen in Table 9, the photoconductors of Examples 33 to 36 were not substantially different therebetween in the half decay exposure amounts and the residual potentials, and showed good surface potential characteristics. The photoconductors of Examples 33 to 35, showed also excellent electrophotographic characteristics for light with a long wavelength of 780 nm. These photoconductors of Examples 33 to 36 can be used for a semiconductor laser printer.

EXAMPLE 37

A photoconductor was produced in the same manner as in Example 5 except that the hydrazone compound No. 105 was used instead of the hydrazone compound No. 5. This photoconductor was charged by corona discharge at −6.0 kV for 10 second and examined with respect to electrophotographic characteristics to obtain good results, namely $V_s = -600$ V, $V_r = -400$ V and $E_{\frac{1}{2}} = 4.0$ lux.sec.

EXAMPLE 38

A photoconductor was produced in the same manner as in Example 6 except that the hydrazone compound No. 106 was used instead of the hydrazone compound No. 6.

The photoconductor thus produced was charged by corona discharge at −6.0 kV for 10 second and examined with respect to electrophotographic characteristics in the same manner as in Example 5 to obtain good results, namely $V_s = -680$ V and $E_{\frac{1}{2}} = 4.3$ lux.sec.

EXAMPLE 39

A photoconductor was produced in the same manner as in Example 7 except that the hydrazone compound No. 107 was used instead of the hydrazone compound No. 7.

The photoconductor thus produced was charged by corona discharge at −6.0 kV for 10 second and examined with respect to electrophotographic characteristics in the same manner as in Example 5 to obtain good results, namely $V_s = -660$ V and $E_{\frac{1}{2}} = 4.8$ lux.sec.

EXAMPLE 40

The photoconductors were prepared in the same manner as in Example 4 but the respective hydrazone compound Nos. 108 to 121 were used as a charge transporting substance. The electrophotographic characteristics of these photoconductors were measured with the testing apparatus SP-428. The results obtained are shown in Table 10. Table 10 shows the half decay exposure amounts $E_{\frac{1}{2}}$ (lux.sec) obtained under the experimental conditions where the photoconductors were positively charged in the dark by corona discharge at +6.0 kV for 10 seconds and irradiated with white light at an illuminance of 2 luxes.

TABLE 10

| Compound No. | $E_{\frac{1}{2}}$ (lux·sec) |
|---|---|
| 108 | 6.1 |
| 109 | 5.2 |
| 110 | 5.4 |
| 111 | 6.5 |
| 112 | 4.8 |
| 113 | 7.3 |
| 114 | 5.5 |
| 115 | 4.9 |
| 116 | 5.2 |
| 117 | 5.5 |
| 118 | 5.9 |
| 119 | 6.4 |
| 120 | 6.0 |
| 121 | 6.1 |

As can be seen in Table 10, the photoconductors using the respective hydrazone compounds Nos. 108 to 121 were satisfactory with respect to the half decay exposure amount $E_{\frac{1}{2}}$.

According to the present invention, since a hydrazone compound represented by any one of the aforementioned chemical formulae is used in a photosensitive layer formed on an electroconductive substrate, as a charge transporting substance, a photoconductor shows a high sensitivity and excellent characteristics in repeated use when adapted to either a positive charge mode or a negative charge mode. A suitable charge generating substance can be chosen so as to be adapted to the kind of exposure light source. By way of example, a phthalocyanine compound a squarylium compound or a bisazo compound can be used as a charge generating substance to provide a photoconductor capable of being used in semiconductor laser printers. If necessary, a covering layer may be provided on the surface of a photoconductor to improve the durability thereof.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. A photoconductor for electrography comprising:
a substrate; and
a photosensitive layer formed on the substrate and containing a charge generating substance and at least one of hydrazone compounds represented by the following general formula (I) as a charge transporting substance;

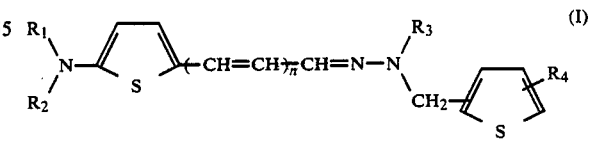

(I)

wherein, each of $R_1$, $R_2$ and $R_3$ stands for any one of an alkyl group, an alkenyl group, an aralkyl group and an aryl group, which groups may be or not may be substituted, $R_4$ stands for any one of a hydrogen atom, a halogen atom, an alkyl group, an alkenyl group, an aralkyl group and an aryl group, which groups may be or not may be substituted and n stands for an integer of 0 or 1.

2. A photoconductor as claimed in claim 1, wherein the photosensitive layer comprises a layer including a dispersion of a charge generating substance and a charge transporting substance selected from hydrazone compounds represented by the general formulae (I) in a binder resin.

3. A photoconductor as claimed in claim 1, wherein the photosensitive layer comprises a laminate of a charge transporting layer including a charge transporting substance selected from hydrazone compounds represented by the general formulae (I) and a charge generating layer.

4. A photoconductor for electrophotography comprising:
a substrate; and
a photosensitive layer formed on the substrate and containing a charge generating substance and at least one of hydrazone compounds represented by the following general formula (II) as a charge transporting substance;

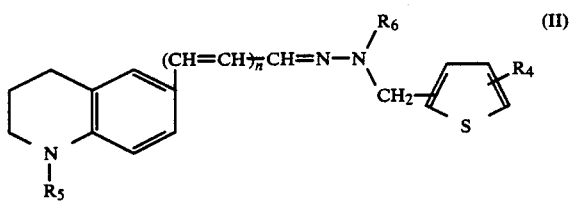

wherein, $R_4$ stands for any one of a hydrogen atom, a halogen atom, an alkyl group, an alkenyl group, an aralkyl group and an aryl group, which groups may be or not may be substituted, $R_5$ stands for any one of a hydrogen atom, an alkyl group, an alkenyl group, an aralkyl group, an aryl group and a thenyl group, which groups may be or not may be substituted, $R_6$ stands for any one of a hydrogen atom, an alkyl group, an alkenyl group, an aralkyl group and an aryl group, which groups may be or not may be substituted and n stands for an integer of 0 or 1.

5. A photoconductor as claimed in claim 4, wherein the photosensitive layer comprises a layer including a dispersion of a charge generating substance and a charge transporting substance selected from hydrazone compounds represented by the general formulae (II) in a binder resin.

6. A photoconductor as claimed in claim 4, wherein the photosensitive layer comprises a laminate of a charge transporting layer including a charge transporting substance selected from hydrazone compounds represented by the general formulae (II) and a charge generating layer.

7. A photoconductor for electrophotography comprising:
a substrate; and
a photosensitive layer formed on the substrate and containing a charge generating substance and at least one of hydrazone compounds represented by the following general formula (III) as a charge transporting substance;

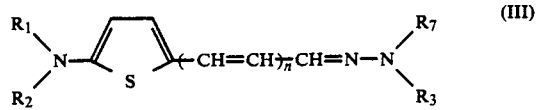

wherein, each of $R_1$, $R_2$, $R_3$ and $R_7$ stands for any one of an alkyl group, an alkenyl group, an aralkyl group and an aryl group, which groups may be or not may be substituted and n stands for an integer of 0 or 1.

8. A photoconductor as claimed in claim 7, wherein the photosensitive layer comprises a layer including a dispersion of a charge generating substance and a charge transporting substance selected from hydrazone compounds represented by the general formulae (III) in a binder resin.

9. A photoconductor as claimed in claim 7, wherein the photosensitive layer comprises a laminate of a charge transporting layer including a charge transporting substance selected from hydrazone compounds represented by the general formulae (III) and a charge generating layer.

10. A photoconductor for electrophotography comprising:
a substrate; and
a photosensitive layer formed on the substrate and containing a charge generating substance and at least one of hydrazone compounds represented by the following general formula (IV) as a charge transporting substance;

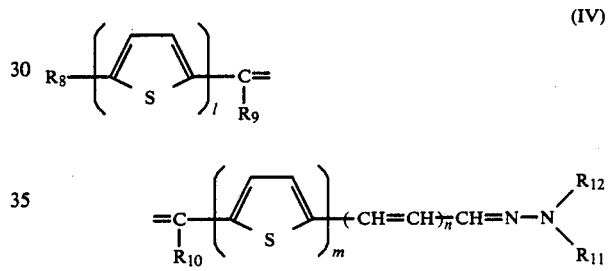

wherein, each of $R_8$, $R_9$ and $R_{10}$ stands for any one of a hydrogen atom, a halogen atom, an alkoxy group, a nitro group, an alkyl group, an alkenyl group, an aralkyl group, an aryl group and an amino group, last five groups of which may be or not may be substituted, each of $R_{11}$ and $R_{12}$ stands for any one of an alkyl group, an alkenyl group, an aralkyl group, an aryl group and a thenyl group, which groups may be or not may be substituted, each of l and m stands for any one of an integer of 1 or 2 and n stands for an integer of 0 or 1.

11. A photoconductor as claimed in claim 10, wherein the photosensitive layer comprises a layer including a dispersion of a charge generating substance and a charge transporting substance selected from hydrazone compounds represented by the general formulae (IV) in a binder resin.

12. A photoconductor as claimed in claim 10, wherein the photosensitive layer comprises a laminate of a charge transporting layer including a charge transporting substance selected from hydrazone compounds represented by the general formulae (IV) and a charge generating layer.

13. A photoconductor for electrophotography comprising:
a substrate; and
a photosensitive layer formed on the substrate and containing a charge generating substance and at least one of hydrazone compounds represented by the following general formula (V) as a charge transporting substance;

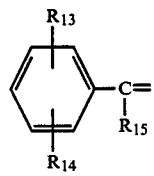 (V)

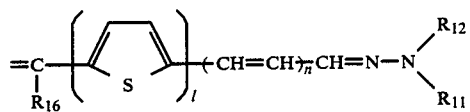

wherein, each of $R_{11}$ and $R_{12}$ stands for any one of an alkyl group, an alkenyl group, an aralkyl group, an aryl group and a thenyl group, which groups may be or not may be substituted, each of $R_{13}$, $R_{14}$, $R_{15}$ and $R_{16}$ stands for any one of a hydrogen atom, a halogen atom, hydroxy group, an alkoxy group, a nitro group, an alkyl group, an alkenyl group, an aralkyl group, an aryl group and an amino group, last five groups of which may be or not may be substituted, l stands for an integer of 1 or 2 and n stands for an integer of 0 or 1.

14. A photoconductor as claimed in claim 13, wherein the photosensitive layer comprises a layer including a dispersion of a charge generating substance and a charge transporting substance selected from hydrazone compounds represented by the general formulae (V) in a binder resin.

15. A photoconductor as claimed in claim 13, wherein the photosensitive layer comprises a laminate of a charge transporting layer including a charge transporting substance selected from hydrazone compounds represented by the general formulae (V) and a charge generating layer.

* * * * *